United States Patent
Oberlin

(10) Patent No.: US 9,469,762 B2
(45) Date of Patent: Oct. 18, 2016

(54) NONAQUEOUS METHOD OF DISPERSING A WATER SOLUBLE POLYMER

(71) Applicant: Rohm and Haas Company, Philadelphia, PA (US)

(72) Inventor: Anne Oberlin, Antibes (FR)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/358,852

(22) PCT Filed: Dec. 11, 2012

(86) PCT No.: PCT/US2012/068902
§ 371 (c)(1),
(2) Date: May 16, 2014

(87) PCT Pub. No.: WO2013/095996
PCT Pub. Date: Jun. 27, 2013

(65) Prior Publication Data
US 2014/0350123 A1    Nov. 27, 2014

Related U.S. Application Data

(60) Provisional application No. 61/579,036, filed on Dec. 22, 2011.

(51) Int. Cl.
| | | |
|---|---|---|
| *A61K 8/14* | (2006.01) | |
| *C08L 71/02* | (2006.01) | |
| *C08J 3/07* | (2006.01) | |
| *C11D 3/20* | (2006.01) | |
| *C11D 3/22* | (2006.01) | |
| *C11D 3/37* | (2006.01) | |
| *A61K 8/73* | (2006.01) | |
| *A61K 8/86* | (2006.01) | |
| *A61K 8/87* | (2006.01) | |
| *A61Q 19/00* | (2006.01) | |
| *C08L 1/28* | (2006.01) | |
| *C08L 75/04* | (2006.01) | |

(52) U.S. Cl.
CPC .................. *C08L 71/02* (2013.01); *A61K 8/14* (2013.01); *A61K 8/731* (2013.01); *A61K 8/86* (2013.01); *A61K 8/87* (2013.01); *A61Q 19/00* (2013.01); *C08J 3/07* (2013.01); *C08L 1/28* (2013.01); *C08L 1/284* (2013.01); *C08L 1/286* (2013.01); *C08L 1/288* (2013.01); *C08L 75/04* (2013.01); *C11D 3/2068* (2013.01); *C11D 3/225* (2013.01); *C11D 3/227* (2013.01); *C11D 3/3707* (2013.01); *C11D 3/3726* (2013.01); *C08J 2301/26* (2013.01); *C08J 2301/28* (2013.01)

(58) Field of Classification Search
CPC ....................................................... A61K 8/14
See application file for complete search history.

(56) References Cited

U.S. PATENT DOCUMENTS

| | | | |
|---|---|---|---|
| 4,325,861 | A | 4/1982 | Braun et al. |
| 4,469,627 | A | 9/1984 | Trombone |
| 4,499,214 | A | 2/1985 | Sortwell |
| 4,799,962 | A | 1/1989 | Ahmed |
| 5,534,182 | A | 7/1996 | Kirk et al. |
| 5,969,012 | A | 10/1999 | Harris |
| 6,818,597 | B2 | 11/2004 | Harris |
| 6,967,027 | B1 | 11/2005 | Heux et al. |
| 2002/0035070 | A1 | 3/2002 | Gardlik et al. |
| 2006/0234890 | A1 | 10/2006 | Griese et al. |

FOREIGN PATENT DOCUMENTS

| | | | | |
|---|---|---|---|---|
| EP | 0002368 | A1 * | 6/1979 | ............... C08J 3/03 |
| EP | 0039128 | B1 | 5/1986 | |
| WO | 97/46606 | | 12/1997 | |
| WO | 01/81476 | A1 | 11/2001 | |
| WO | 2013/095996 | A1 | 6/2013 | |
| WO | 2014/062379 | | 4/2014 | |

OTHER PUBLICATIONS

Rohm and Hass Co (Acusol Rheology Modifiers, 2009, 1-16).*
ACUSOL™ Rheology Modifiers, Rohm and Haas Company 2003, pp. 1-16.

* cited by examiner

*Primary Examiner* — Benjamin Packard

(57) ABSTRACT

Described are methods of dispersing and hydrating a water soluble polymer, comprising forming a nonaqueous slurry of polypropylene glycol, water soluble polymer, and hydrophobically modified ethoxylated urethane, provided that the slurry contains less than five percent water; and then contacting the nonaqueous slurry with water to disperse and hydrate the water soluble polymer.

8 Claims, No Drawings

NONAQUEOUS METHOD OF DISPERSING A WATER SOLUBLE POLYMER

CROSS REFERENCE TO RELATED APPLICATIONS

This application is a 35 USC §371 national phase filing of PCT/US2012/068902 filed Dec. 11, 2012, which claims the benefit of U.S. Application No. 61/579,036, filed Dec. 22, 2011.

FIELD

The present invention relates to methods and compositions for dispersion of water soluble polymers.

BACKGROUND

Many water soluble polymers (cellulose, cellulose derivatives, gums, and the like) are typically sold in solid, dry, form, and hence powder handling and processing properties are extremely important. For example, a low dust content is desirable. Also, the ability of the dry powder to be poured from a container or receptacle is described as flowability. Flowability is affected by particle shape and size distribution, and resulting bulk density. Bulk density is the mass of powdered solid material per unit of volume occupied. Acceptable flowability generally depends upon relatively high bulk density and relatively low angle of repose. The angle of repose is the maximum angle between the slope of a conical discharged pile of powder and the surface it rests upon, a lower angle representing a more widely spread pile.

As part of using the water soluble polymer in its various applications, the water soluble polymer must be dissolved. Dissolution is frequently described as a process with two overlapping phenomena, dispersion and hydration. Dispersion refers to spreading of particles or groups of polymer chains throughout the solution. Hydration refers to loosening of the polymer chains and expansion of their hydrodynamic volume (and corresponding viscosity buildup). If dispersion is poor, or if hydration outpaces dispersion, hydrated polymer can swell and isolate relatively dry, non-hydrated polymer from the solution, forming lumps. Desirable dispersion and hydration are normally characterized by little to no lump formation and a rapid viscosity build up over time, respectively.

Accordingly, there is a need in the industry to reduce the foregoing problems (dust, variable flow, inconsistent dispersion, or undesirable rate of hydration) in order to simplify formulation of products incorporating water soluble polymers.

DETAILED DESCRIPTION

In one embodiment, the present invention provides a method of dispersing and hydrating a water soluble polymer, comprising forming a nonaqueous slurry of polypropylene glycol, water soluble polymer, and hydrophobically modified ethoxylated urethane, provided that the slurry contains less than five percent water; and then contacting the non-aqueous slurry with water to disperse and hydrate the water soluble polymer.

The term "polypropylene glycol" means an oxygenated solvent or polyol that has at least three units of propylene glycol. It is contemplated that the polypropylene glycol may also include methyl ether and/or propyl ether units in its composition, and/or be a polyglycol copolymer of ethylene oxide and propylene oxide. The molecular weight (MW) of the polypropylene glycol is between 148 g/mol and 5000 g/mol, preferably 206 g/mol to 400 g/mol. In one embodiment, the polypropylene glycol is POLYGLYCOL P-400 E (CAS #: 25322-69-4) or DOWANOL TPM (Tripropylene Glycol Methyl Ether, CAS #: 25498-49-1) from The Dow Chemical Company.

In one embodiment, the water soluble polymer is at least one water-soluble, film-forming natural and synthetic polymers including alkylcellulose ethers, hydroxyalkyl cellulose ethers and hydroxyalkyl alkylcellulose ethers, including methylcellulose; hydroxypropyl methylcellulose (HPMC); hydroxyethyl methylcellulose (HEMC); hydroxyethyl cellulose (HEC); hydroxypropyl hydroxyethylcellulose (HPHEC) and hydroxypropylcellulose (HPC), water-soluble, high molecule weight polymers of ethylene oxide, preferably of about 20,000 molecular weight or higher; natural products such as guar gum, xanthan gum and water-soluble thickening agents. Preferably, the water soluble polymer is a water soluble modified cellulose ether selected from the group consisting of: alkyl cellulose derivatives, hydroxyalkyl cellulose derivatives, cationic hydroxyalkyl cellulose derivatives (the cationic specie being a quaternary alkyl amine) and carboxylalkyl cellulose derivatives. In one embodiment, the water soluble modified cellulose ether is not a hydration-retarded (surface-treated) grade. Preferred water soluble polymers are hydroxyethyl cellulose (available under the tradename CELLOSIZE from The Dow Chemical Company), cationically-modified hydroxyethylcellulose (cat-HEC), hydroxypropylmethylcellulose (available under the tradename METHOCEL from The Dow Chemical Company), and polyethylene oxide (available under the tradename POLYOX from The Dow Chemical Company).

Hydrophobically modified ethoxylated urethane (HEUR) has a MW between 20,000 to 80,000 g/mol. In one embodiment, the hydrophobically modified ethoxylated urethanes is ACUSOL™ 880 from the Dow Chemical Company.

In one embodiment, the non aqueous slurry has less than 4%, preferably less than 3%, and more preferably less than 2% water.

In one embodiment, the present invention provides a non aqueous slurry consisting essentially of polypropylene glycol, water soluble polymer, and hydrophobically modified ethoxylated urethane, provided that the slurry contains less than five percent water. In one embodiment, the non aqueous slurry is phosphate free. In one embodiment, the non aqueous slurry is oil free. In one embodiment, the non aqueous slurry is surfactant free.

The present invention speeds dissolution of water soluble polymers in water, and accordingly finds use in personal care and fabric care applications, where water soluble polymers are hydrated and incorporated into personal care or fabric care formulations. In one embodiment, formulation time is decreased due to faster dissolution.

EXAMPLES

Example 1

A nonaqueous slurry of the present invention is described in TABLE 1 in weight percent:

TABLE 1

|  | Batch 1 | Batch 2 | Batch 3 | Batch 4 | Batch 5 | Batch 6 |
|---|---|---|---|---|---|---|
| POLYGLYCOL P-400 E polypropylene glycol | 72.3 | 72.3 | 72.3 | 72.3 | 72.3 | 72.3 |
| Acusol 880 (35% active) hydrophobically modified ethoxylated urethane | 7.7 | 7.7 | 7.7 | 7.7 | 7.7 | 7.7 |
| CELLOSIZE QP100MH hydroxyethyl cellulose | 20 | — | — | — | — | — |
| CELLOSIZE WP3000 hydroxyethyl cellulose * | — | 20 | — | — | — | — |
| Cationic hydroxyethyl cellulose | — | — | 20 | — | — | — |
| Cationic hydroxyethyl cellulose * | — | — | — | 20 | — | — |
| METHOCEL 40-202 HPMC | — | — | — | — | 20 | — |
| POLYOX WSR N80 Polyethylene oxide | — | — | — | — | — | 20 |

* surface treated

At room temperature, polypropylene glycol in a 200 mL plastic beaker is stirred at 500 rpm (Heidolph RZR 2020 agitator from Heidolph, Germany and a four square blades propeller, from KA Werke, Germany). Then, hydrophobically modified ethoxylated urethane is added under agitation at 500 rpm and stirred until completely dissolved, forming an opalescent mixture. Still under 500 rpm agitation, the water soluble polymer is added slowly, and the agitation continued at 500 rpm for 10-15 minutes to form a non-aqueous slurry.

Example 2

Batches 1-6 were made substantially according to Example 1, and tested. Visually, the six formulations presented no phase separation after 1 week of storage either at room temperature, 4° C., or 40° C.

Batch 3 was selected for further characterization, viscosity using a Brookfield DV III Ultra programmable rheometer, with the spindle #64, as shown in TABLE 2:

TABLE 2

|  | rpm | 6 | 3 | 6 | 12 | 30 | 60 |
|---|---|---|---|---|---|---|---|
| Day 1 22.5° C. | viscosity (cPs) | 59 000 | 14 200 | 8 200 | 4 950 | 2 560 | 1 690 |
|  | % torque | 5.9 | 7.1 | 8.2 | 9.9 | 12.8 | 16.9 |
| +4 weeks 23.5° C. | viscosity (cPs) | 60 000 | 10 000 | 6 350 | 3 440 | 3 440 | 2 280 |
|  | % torque | 6 | 8.4 | 10.1 | 12.7 | 17.2 | 22.8 |

After 4 weeks, Batch 3 still had no phase separation and the viscosity indicates the slurry is stable.

Example 3

Batches 1-5 were made substantially according to Example 1, and tested for dissolution versus the corresponding untreated water soluble polymer, all at 2% concentration. Results are presented in TABLE 3.

TABLE 3

| | Observations |
|---|---|
| Batch 1 | Good: homogeneous, opalescent |
| Batch 2 | Good: homogeneous, opalescent |
| Batch 3 | Good: homogeneous, opalescent |
| Batch 4 | Good: homogeneous, opalescent |
| Batch 5 | Good: homogeneous, opalescent |

TABLE 3-continued

| | Observations |
|---|---|
| Comparative CELLOSIZE QP100MH hydroxyethyl cellulose | Poor: opaque |
| Comparative CELLOSIZE WP3000 hydroxyethyl cellulose * | Poor: opaque |
| Comparative Cationic hydroxyethyl cellulose | Failed: gel formation |
| Comparative Cationic hydroxyethyl cellulose * | Failed: gel formation |
| Comparative METHOCEL 40-202 HPMC | Failed: gel formation |

10 g of each inventive slurry listed (effectively containing 2 g of water soluble polymer) were placed in 90 g deionized water and agitated 2 min (after polymer addition) at 500 rpm using an Overhead agitator, Heidolph RZR 2020 from Heidolph, Germany.

2 g of the listed conventional cellulose ethers were placed in 98 g deionized water and agitated 2 min (after polymer addition) at 500 rpm using an Overhead agitator, Heidolph RZR 2020 from Heidolph, Germany.

Each solution was evaluated by a trained panelist for evidence of dissolution problems known to those skilled in the art (fish-eyes, gel formation, opaqueness). The conclusion was that the present invention offered faster and easier dissolution.

The invention claimed is:

1. A method of dispersing and hydrating a water soluble polymer, comprising:
   forming a slurry of polypropylene glycol, water soluble polymer, and hydrophobically modified ethoxylated urethane, provided that the slurry contains less than five percent water and that the slurry is surfactant free; and then
   contacting the slurry with water to disperse and hydrate the water soluble polymer.

2. The method of claim 1, wherein the water soluble polymer is a water soluble modified cellulose ether selected from the group consisting of: alkyl cellulose derivatives, hydroxyalkyl cellulose derivatives, cationic hydroxyalkyl cellulose derivatives (the cationic specie being a quaternary alkyl amine) and carboxylalkyl cellulose derivatives.

3. The method of claim 1, wherein the water soluble polymer is selected from the group consisting of: hydroxyethyl cellulose, cationically-modified hydroxyethylcellulose, hydroxypropylmethylcellulose, and polyethylene oxide.

4. The method of claim 1, wherein the method is performed without addition of heat.

5. The method of claim 1, wherein the polypropylene glycol is Tripropylene Glycol Methyl Ether.

6. A slurry consisting essentially of:
   polypropylene glycol,
   water soluble polymer, and hydrophobically modified ethoxylated urethane,
provided that the slurry contains less than five percent water and that the slurry is surfactant free.

7. A personal care composition containing water soluble polymer, formed by the method of claim 1.

8. A fabric care composition containing water soluble polymer, formed by the method of claim 1.

* * * * *